United States Patent [19]

Merav

[11] 3,995,643
[45] Dec. 7, 1976

[54] INTRATRACHEAL TUBE

[76] Inventor: Abraham D. Merav, 5800 Arlington Ave., Riverdale, N.Y. 10471

[22] Filed: Jan. 13, 1975

[21] Appl. No.: 540,454

[52] U.S. Cl. .............................................. 128/351
[51] Int. Cl.² ................ A61M 16/00; A61M 25/02
[58] Field of Search ....... 128/208, 245, 348, 349 B, 128/351

[56] References Cited
UNITED STATES PATENTS

| | | | |
|---|---|---|---|
| 3,173,418 | 3/1965 | Baran | 128/351 |
| 3,616,799 | 11/1971 | Sparks | 128/351 |
| 3,709,227 | 1/1973 | Hayward | 128/351 |
| 3,769,983 | 11/1973 | Merav | 128/351 |

Primary Examiner—Channing L. Pace
Attorney, Agent, or Firm—J. David Dainow

[57] ABSTRACT

A device for intubation of the tracheal passage comprising a tube through which gas can be administered and an occlusion means to seal the annular space around the tube when it is positioned in a tracheal passage. The occlusion means is formed as a canopy of flexible material having a top part traversed by said tube in an air-tight junction with an inflatable annular chamber extending around the wall of the canopy. Inflation of this chamber distends the canopy against the tracheal wall and simultaneously creates a second annular chamber between the inner surface of the canopy and the outer surface of the tube. The bottom of the canopy is open during positive pressure ventilation, for allowing an upward flow of gas via the annular space into said second chamber to inflate and distend the canopy against the tracheal wall independently of inflation of said first annular chamber.

20 Claims, 16 Drawing Figures

INTRATRACHEAL TUBE

BACKGROUND OF THE INVENTION

This invention relates to apparatus for use in artifical respiration, and particularly to intratracheal tubes used during surgical procedures and in ventilatory support of critically ill patients.

Modern respiratory support of patients and modern anesthesia procedures often require administration of air, oxygen or other gases into the lungs under positive pressure, as provided by apparatus such as respirators, anesthesia machines, or manually compressed balloons. For conducting the gas to a patient's lungs, a tube is generally inserted into the trachea either through the mouth, the nose, or via a surgically created opening in the neck in a tracheostomy procedure; the corresponding intratracheal tubes for the above intubations are referred to as endotracheal, nasotracheal or tracheostomy tubes. A pulsating supply of the pressurized gas from an external source is directed down through the intratracheal tube where it forces a rhythmic expansion of the lungs. Such intubation is especially advantageous when a patient is unable to provide even the minimum muscular activity to sustain breathing.

The typical intratracheal tube has an outer diameter smaller than the inside diameter of the tracheal passage into which it is inserted which facilitates the intubation, but results in an annular space between the tube and the inner lining of the trachea. In order to artificially inflate the lungs with positive pressure, an air-tight seal must be established in this annular space, or else air pumped down the tube toward the lungs will escape upward through this space. Conventional means for achieving such a seal include various inflatable "cuffs", which have appearance similar to miniature inflated inner-tubes for tires. Such a cuff is attached to and surrounds a tube, and when inflated the cuff extends radially outward from the tube until it contacts the tracheal wall, thus filling the annular space. A cuff is inflated only after its tube is inserted into the trachea, and then by injection of air, gas or other fluid through a small conduit. An additional important reason for the above-described cuff seal is the prevention of aspiration, i.e. the passage through this annular space into the lungs of liquids or solids from the upper airway or from the mouth. This problem is particularly serious with unconscious patients who may tend to aspirate vomited material or other oral secretions.

In recent years it has become evident that tracheal walls have been damaged by an inflated cuff, where the lateral pressure exerted by the cuff against the mucosal lining of the trachea was prolonged and/or excessive. The recent medical literature is replete with studies and surveys of tracheal stenosis, tracheomalacia, ulceration, erosion of the tracheal wall, and the formation of lesions resulting from the prolonged intubation with intratracheal tubes. In the vast majority of such complicating diseases and injuries, which are often worse than the respiratory illness itself or other original cause for using the intratracheal tube, the cause of said secondary problems has been traced directly to the employment of the cuff and the prolonged tracheal wall pressure required for its use. A partial tabulation of such studies, includes the following articles: Carrol and Hedden, Journal of Anesthesiology, September, 1969, Vol. 31, No. 3, pages 275 – 281; Catane et al, British Journal of Anaesthesiology, 1969 Vol. 41, page 1086; Grillo, H.C. Journal of Thoracic and Cardiovascular Surgery, January 1969, Vol. 57, No. 1 page 52; Shelly et al. Journal of Thoracic and Cardiovascular Surgery, May 1969, Vol. 57, No. 5 page 623; Fishman et al. Annals of Thoracic Surgery, July 1969, Vol. 8, No. 1, page 47; Miller et al. Annals of Surgery, Feb. 1970, Vol. 171, No. 2, page 283; and Westgate et al. Anesthesia and Analgesia, May-June 1970, Vol. 49, No. 3, page 393.

The results of the studies and findings in this field lead to the conclusion, that while intratracheal support of ventilation is often necessary, there is a need for an improved, less harmful intratracheal tube with means for occluding the tracheal passage, and efforts in this direction have produced further analytical data on the mechanical operation of these devices. As indicated above conventional cuffs require pressures and volumes of substantially high magnitude to produce sufficient lateral or tracheal wall pressure to maintain the cuff in sealing condition against the wall of the trachea. This lateral pressure is at least equal to the highest peak pressure reached in the lungs below the cuff during the artifical inflation of said lungs. Consequently, with these conventional cuffs, the tracheal wall pressure becomes generally significantly greater than the pressure sustaining capillary blood flow, so that blockage of blood flow through the mucous lining (ischemia) occurs. Not even the standard procedure of deflating the cuff for a few minutes or so every hour successfully overcomes this problem.

The above problems are accentuated when one appreciates the fact that since the intubation is hidden from view of the doctor or surgeon, accurate measurement of the pressure is not feasible. It is thus not uncommon, in order to insure an airtight seal, that an operator will set the cuff and tracheal wall pressure at levels greater than that actually necessary for the secure occlusion of the trachea.

With the hope of decreasing the lateral pressure against the tracheal wall, certain parachute or canopy shaped cuffs have been developed which differ from "inner tube" or "balloon" cuffs in that they do not require external inflation, i.e. from a source of air under pressure. In place of the balloon is a parachute-like member with its open end directed downward and its dome traversed by the tube extending axially therethrough. An air flow, during the positive pressure phase of respiration, downward through the tube and tending to escape upward via the annular space in the tracheal passage, will collect under the parachute dome, and inflate same until the body of the parachute is distended into pressure contact with the tracheal lining. The degree of distention depends on the volume and pressure of this upward gas flow; however, the lateral pressure which these cuffs exert on the tracheal wall is no greater than, and virtually equals the pressure which exists in the airway below or distal to the cuff at any given moment. Accordingly the duration and magnitude of this pressure is only the minimum required for achieving the airway seal, as contrasted to an arbitrary high pressure of balloon cuffs inflated from an independent and external source. Thus with these parachute cuffs it is essentially impossible to injudiciously or accidentally overinflate, since the external gas source has been eliminated. Illustrations and further description of these earlier parachute cuffs are found in the U.S. Pat. No. 3,769,983 issued on Nov. 6, 1973 to A.D. Merav, the inventor in the present application, and in article "Pressures of Tracheostomy Cuffs in Ventilated Patients", New York Journal of Medicine, Aug. 15, 1971, p.p. 1923–1928.

Unfortunately these parachute-type cuffs are not totally satisfactory. While they achieve an airway seal under conditions of positive-pressure ventilation, and are especially well-suited for prolonged intubation in patients who are conscious and do not tend to aspirate, they do not seal the airway when the patient breathes in spontaneously, at which time he may aspirate liquids or solids. Because of this real and frequent danger with these known parachute cuffs, many surgeons are reluctant or simply refuse to use them, and instead use the standard balloon cuffs with their inherent disadvantages.

It is an object of the present invention to provide an occulusive intratracheal cuff which can create an airway seal that is continuous and sufficient to prevent aspiration, and yet will not exert a continuous high pressure against the tracheal wall, and will thus eliminate the ancillary problems caused by said excessive tracheal wall pressure common with use of balloon cuffs.

SUMMARY OF THE INVENTION

The invention provides an intratracheal tube with a novel occulusion means for sealing the annular space between the outer surface of the tube and the inner surface of a tracheal passage wall. This occulusion means is formed as a parachute or canopy of flexible material having a top part including therein an aperture traversed by said tube, the aperture defining a top edge secured to the outer surface of the tube in an air-tight seal at a first axial position thereon. The canopy further comprises a body part extending from said top edge and terminating in a distal edge, with an inflatable, annular chamber formed in or on said body part. Inflation of this chamber from an external source of fluid distends the canopy outward from the tube to contact and seal against the tracheal wall. Such distention creates within the canopy a second, inner annular chamber situated between the outer surface of the tube and the inner surface of the canopy and having an open bottom for allowing an upward flow of gas into the annular space to collect in this second chamber, and inflate and distend the canopy against the tracheal wall, independently of inflation of said first or outer annular chamber.

While the dome of a distended canopy may be either concave or convex relative to the top edge thereof, the distal edge of the canopy is directed downward toward and radially spaced from said tube, and has diameter greater than said tube, thus defining an annular, open bottom end. Alternatively this distal edge can be secured to the tube, but have apertures for said upward gas flow to inflate the inner annular chamber within the canopy. In further alternative structures said outer annular chamber may be located near the top edge of the canopy, or near the distal edge, or extending between said two edges, or elsewhere on the body of the canopy. It is also to be emphasized that since a tracheal passage in cross-section is not exactly circular, the terminology "annular" regarding cuffs for occluding this passage, should be understood to mean any cuff having an outer peripheral surface that is generally round, and thus may be circular, ellipticul, irregular, or other generally closed curve surfaces. This broad definition of "annular" should also be used in interpreting the claims.

Where the distal edge is free, it is preferable to utilize flexible restraining means of generally fixed maximum length interconnecting said edge and the tube at a second position on the tube axially distal of the first position for restraining the distal edge from axial movement toward the proximal end and away from said second position, any distance greater than said fixed length.

Other embodiments and features of this invention are described below with reference to the drawings illustrating said invention.

BRIEF DESCRIPTION OF THE DRAWINGS

FIG. 4 is a fragmentary view, in section of a second embodiment of the device shown in FIG. 2, FIGS. 5–9 are views similar to FIG. 4 illustrating third, fourth, fifth, sixth and seventh embodiments of said device.

DETAILED DESCRIPTION OF THE PREFERRED EMBODIMENTS

Figure 1:
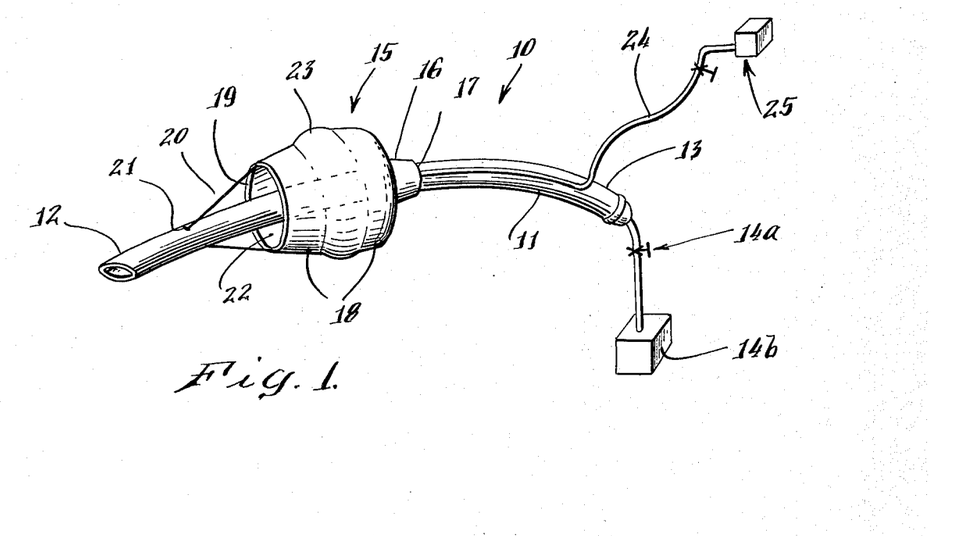
FIG. 1 is a perspective view of a preferred embodiment of the new intratracheal tube.

FIG. 1 of the drawings shows a new endotracheal tube 10 of this invention comprising a central tube 11 having a first end 12, designated distal or inferior or remote end, with a slanted edge for ease of insertion into the tracheal passage, and a second end 13, designated proximal or superior or near end, which is connectible via a conduit and metering means 14a shown schematically, to a source of pressurized gas 14b which may be air and will be so designated hereafter merely for convenience. Tube 11 may be made of a flexible or semi-flexible material, such as rubber, polyvinyl-chloride (PVC), or other plastic or even metal. The length and diameter of tube 11 can vary to fit different trachea; also the nature of the air source can vary, so long as this source includes means for selectively delivering a periodic or pulsating air flow of regulated pressure and volume.

Figure 2:
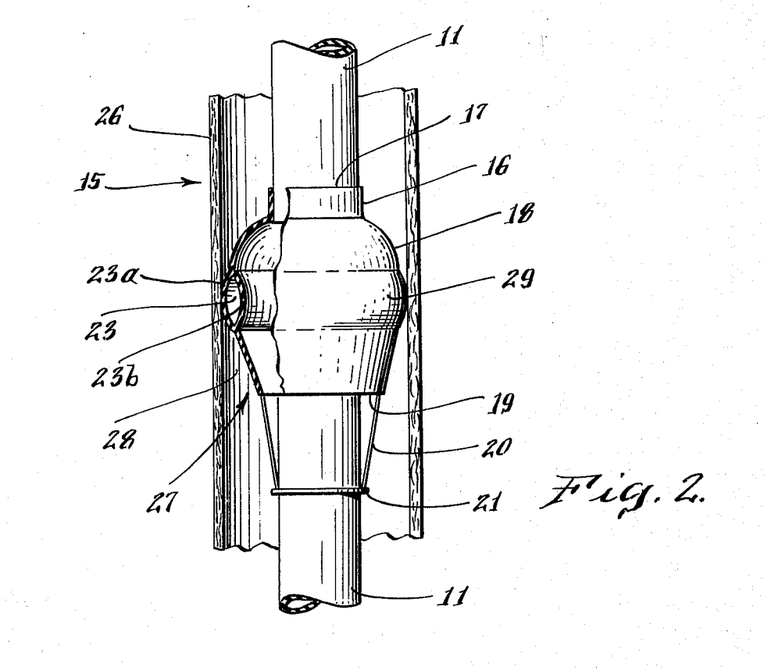
FIG. 2 is a partial elevation view in section, of the embodiment of FIG. 1, shown in operable inflated condition within a portion of a tracheal passage.

The new cuff 15 is shown intermediate the two ends of the tube 11, and formed generally as a canopy or parachute with a top edge 16 secured to the tube at first axial position 17 in an air-tight seal, and a body part 18 extending from said top edge and terminating in bottom edge 19. Restraining means 20 interconnect this edge 19 to the tube 11 at a second axial position 21 located distal of the first position 17. Within and defined by the body part 18 is an inner annular chamber 22, and surrounding the body part is an outer annular chamber or pocket 23. Through conduit 24 air or other fluid may be conducted under pressure from a source 25 to said chamber 23 for inflating same to form the outer annular chamber and thereby distend the canopy. A soft, flexible material is used for the canopy, such as very thin surgical rubber or silicon rubber sold under the trademark, SILASTIC of Dow-Corning Corp.. The material must be sufficiently flexible to readily conform to the shape of the tracheal passage and seal quickly and securely thereagainst with a minimum of lateral pressure. The shape of the cuff may be generally oval as shown in the FIGURES, or spherical, or cylindrical or conical, or some variation that will occlude the passage when distended. FIG. 2 shows the device of FIG. 1 located within a tracheal passage 26, with annular space 27 defined between tube 11 and the tracheal lining 28. Upon inflation of pocket 23, layers 23a and 23b separate and define between them the outer annular chamber, which then occludes and seals the annular space 27, as lateral pressure contact with the tracheal lining is established.

Figure 3A:
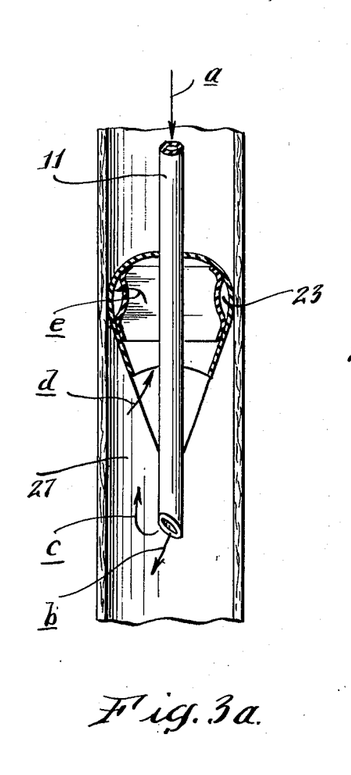
FIGS. 3a, 3b and 3c are partial elevation views in section showing schematically the operation of the device of FIG. 1.

As will be described in later portions of this description, the exact shape and location of the outer annular chamber on the canopy may vary considerably; however the function of the cuff remains substantially the same, this function being illustrated schematically in FIGS. 3a, 3b, and 3c. In FIGS. 3a air flows under pressure down tube 11, indicated by arrow a, during the positive pressure inspiration phase of ventilation, and to the lungs, indicated at b. Air at c tries to escape upward through annular space 27, but upon entering the open bottom of the canopy at d, this air inflates and distends the canopy, creating the lateral pressure seal at e. It should be apparent that the pressure at e is no greater than the pressure at b and in the lungs, which is a significant advantage of standard parachute cuffs.

Figure 3B:
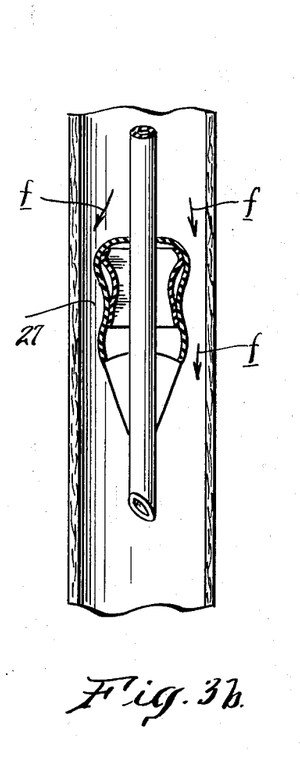

FIG. 3b shows the cuff in a partially collapsed condition which can occur when a patient breathes in spontaneously; air pressure below the canopy becomes less than atmospheric, and air flows at f in the annular space 27 past the cuff. It is in this condition, with space 27 no longer occluded, that aspiration of liquids and/or solids from the upper airway can occur. In both FIGS. 3a and 3b the outer annular chamber 23 is uninflated and flacid, which demonstrates how the cuff can be self-inflating as in FIG. 3a, and how such inflation is not always a reliable seal, as in FIG. 3b.

Figure 3C:
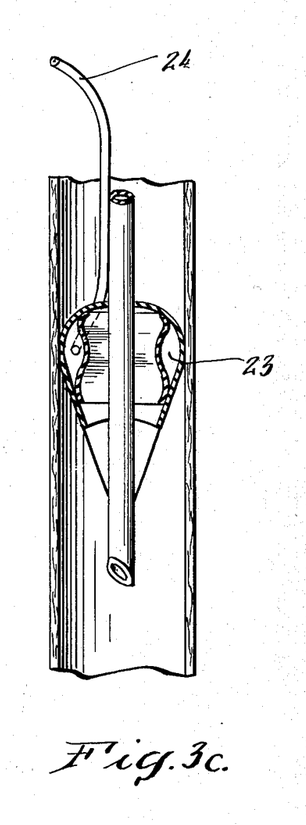

FIG. 3c shows the same cuff with chamber 23 inflated to distend the canopy into lateral pressure contact with the tracheal lining, this pressure being sufficient to prevent aspiration, but not as great as in a standard balloon cuff which cannot benefit from self-inflation as provided by the parachute feature shown in FIG. 3a.

Figures 4, 6:
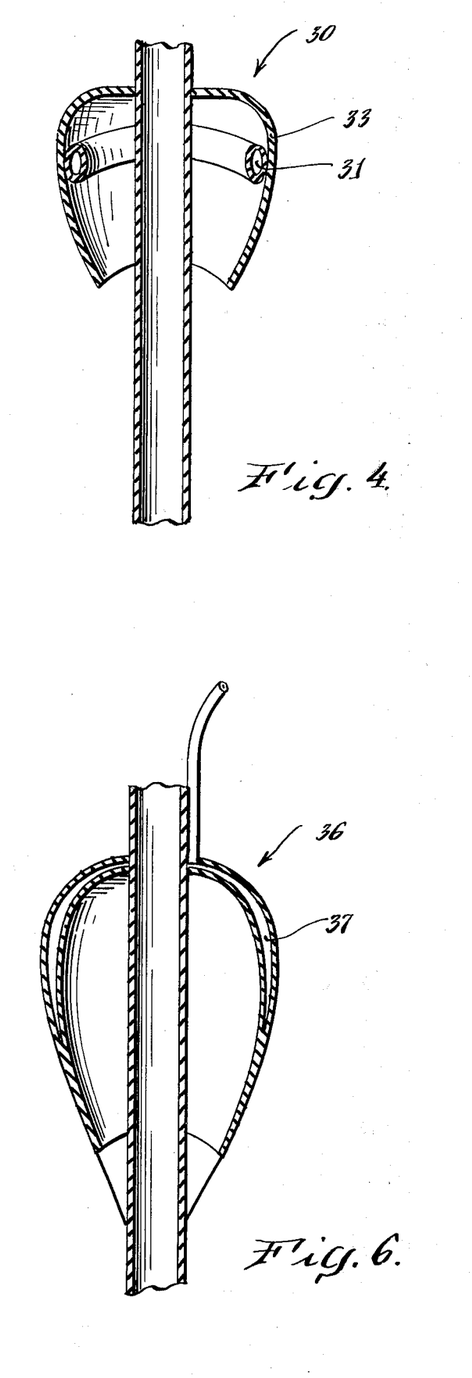
Figures 5, 7:
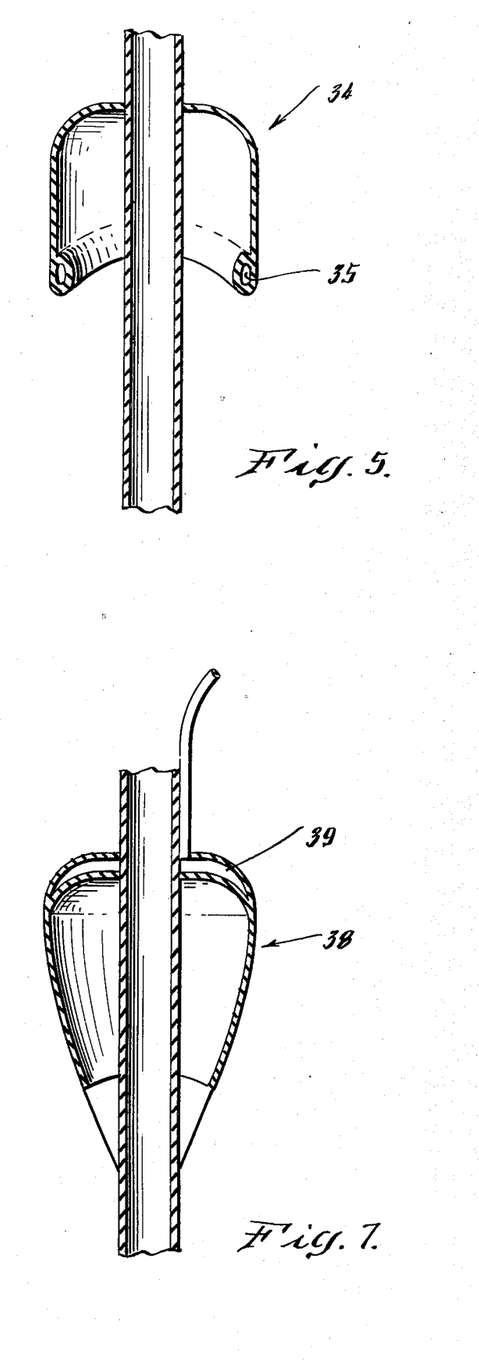
Figure 8:
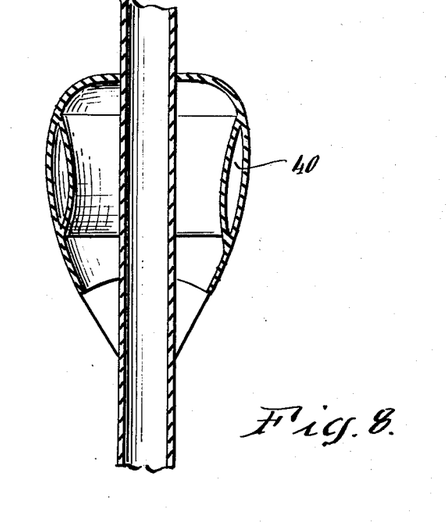
Figure 9:
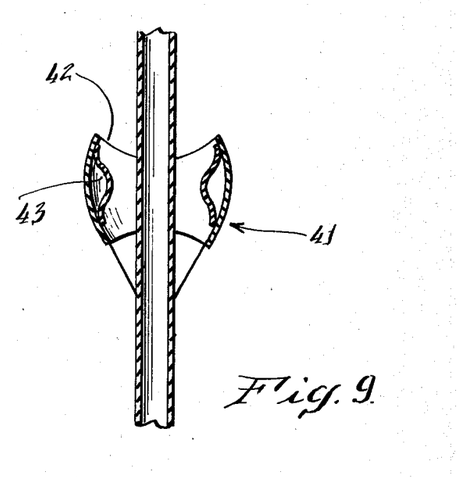
Figure 11:
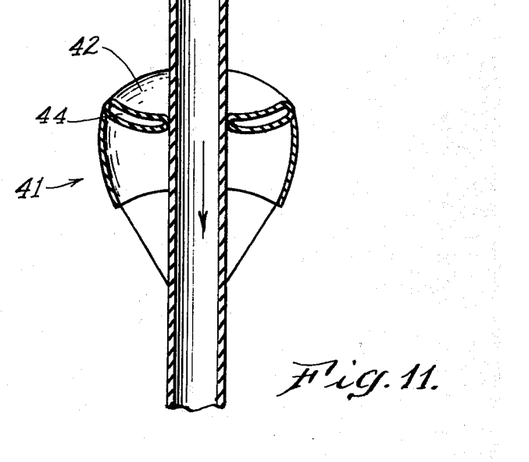
FIG. 11 is a fragmentary view, in section of a further embodiment having openings in the tube wall for inflation of the parachute instead of in the bottom of the cuff.

FIG. 4 shows a different embodiment of the invention namely an intratracheal tube and cuff 30 similar to that of FIG. 2, except that the outer annular pocket 31 comprises a separate annular tube secured to the body part 33 of the cuff, as contrasted to a double-wall portion 23 in FIG. 2. FIG. 5 shows a cuff 34 of another embodiment, with the outer annular pocket 35 at the bottom or terminal edge of the canopy. FIG. 6 shows a different cuff 36, wherein the entire canopy is double-walled, so that the outer annular chamber 37 is like a full length shell. FIG. 7 shows another cuff 38 with the annular pocket 39 located at the top of the canopy. In FIG. 8 the annular chamber 40 is elongated, with axial length substantially greater than the radial dimension. FIGS. 9 and 11 show a cuff 41 which differs from preceeding cuffs in that the dome 42 of the canopy is concave; the inflatable pocket may be located around the outer circumference as indicated at 43 in FIG. 8 or at the top as indicated at 44, in FIG. 11 or elsewhere as shown in previous Figures. An inverted dome, as shown here, may be advantageous in collecting liquids which might otherwise tend to leak past the seal.

Figure 10:
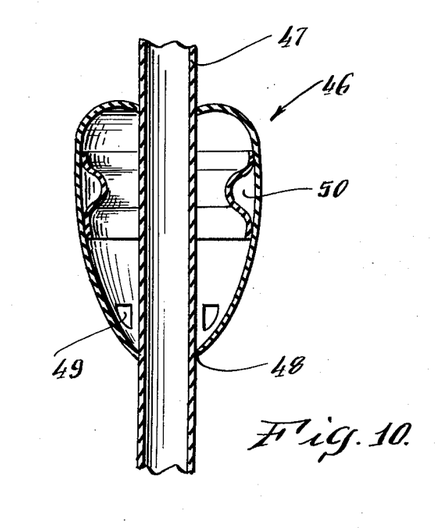
FIG. 10 is a fragmentary view, in section of a still different embodiment of this invention, having apertures in the bottom instead of an opening.

FIG. 10 shows a different version 46 of the new cuff. Instead of strand-like restraining means 20 shown in FIG. 2, the body part of this cuff extends all the way down to the tube 47 and is secured there at axial position 48. Apertures 49 allow upward air flow for self-inflation of the canopy, and the outer annular chamber 50 is provided as in the previous embodiments.

Figure 12A:
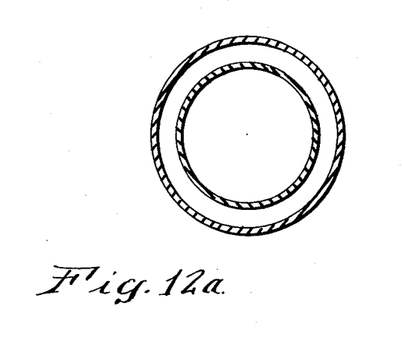
FIGS. 12a – 12c show sectional plan views of three different outer annular chambers for the new invention.
Figure 12B:
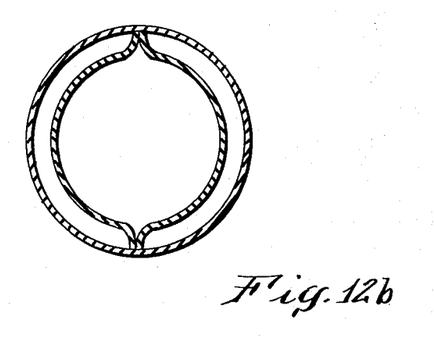
Figure 12C:
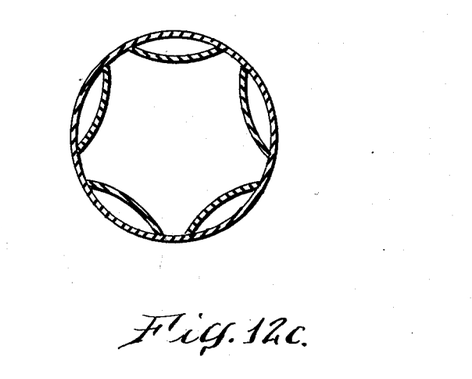

Furthermore, the many outer annular chambers shown in FIGS. 1–11 may vary in sectional plan view, as shown in FIGS. 12a–12c: the chamber is continuous in FIG. 12a, is segmented in FIG. 12b, is intermittant in FIG. 12c, or may have still other shapes which will, when inflated, constitute inflatable means to distend the canopy's outer peripheral surface away from the central tube, and into a generally circular shape for contact with the trachea.

The new device in any of the above embodiments, will provide the desired seal in the tracheal passage against aspiration and permit prolonged intubation without excessive or constantly high lateral pressure on the tracheal lining. Accordingly, this represents a significant advance over (a) balloon cuffs which are used despite the very serious deleterious side effects, and (b) plain parachute cuffs which are avoided because they are not reliable to prevent aspiration.

The above-described structures are presented as preferred embodiments, with the understanding that variations in structure are quite possible, while remaining within the scope of the invention.

I claim:

1. A device for intubation of a tracheal passage and operable with an external source of fluid with a gas flow outward through said passage from the lungs to the atmosphere, the device comprising a tube having a diameter less than that of a normal tracheal passage and having a distal end for insertion into said tracheal passage and an opposite proximal end, and a canopy of flexible material which is both distendible to a generally annular shape for sealing the space between the tube and the passage and also is collapsible, the canopy having a top part including therein an aperture traversed by said tube, the aperture defining a top edge secured to the outer surface of said tube in an air-tight seal at a first axial position thereon, and also having a body part extending from said top edge and terminating in a free distal edge, said body part further including inflatable first chamber means for distending said canopy to a generally annular shape which, when distended, defines a dome opening toward the distal end, and within said dome a second generally annular chamber, with said distal edge of the canopy being radially spaced from the tube and having diameter greater than the outer diameter of the tube adjacent thereto and thus defining an open distal end of said canopy, said device further comprising inflation means for communicating said source of fluid to said first chamber means for inflating same and thereby distending said canopy, into said dome shape, said canopy also being distendible by said gas flow entering the canopy via said distal end thereof and filling said second chamber, which thereby distends said canopy into said dome shape, said first and second chambers being inflatable both jointly, and independently of each other, for distending said canopy.

2. A device according to claim 1 wherein said first chamber means comprises a single pocket.

3. A device according to claim 2 further comprising restraining means of generally fixed maximum length interconnecting said distal edge and said tube at a second position on the tube axially distal of said first position, for restraining said distal edge from axial movement toward the proximal end and away from said second position, any distance greater than said fixed length.

4. A device according to claim 2 wherein said tube, canopy, first and second chambers are generally coaxial.

5. A device according to claim 2 wherein said first chamber is a portion of said canopy body part comprising at least two layers of said flexible material, which layers become spaced apart when said first chamber is inflated.

6. A device according to claim 5 wherein said canopy has a proximal part extending from said top edge partway toward said distal edge, a distal part extending from said distal edge partway toward said proximal edge, and a medial part intermediate said proximal and distal parts, and said first chamber coincides with at least one of said proximal, medial, and distal parts.

7. A device according to claim 6 wherein said first chamber coincides with said proximal part and forms the dome of said canopy.

8. A device according to claim 1 wherein said first chamber means comprises a plurality of pockets.

9. A device according to claim 1 wherein said inflation means comprises a second tube that has a first end communicating with said first chamber and a second end connectible to said external source of fluid.

10. A device according to claim 9 wherein said external source of fluid comprises a container with a premeasured quantity of said fluid therein, which is sufficient to inflate said first chamber, when it is conducted to said chamber.

11. A device according to claim 1 wherein said distal edge is always distal to said top edge.

12. A device according to claim 1 wherein said first chamber comprises flexible material forming an inflatable annular ring generally coaxial with said tube and secured to said body part of the canopy.

13. A device according to claim 3 wherein said restraining means comprises a plurality of strands spaced apart circumferentially.

14. A device according to claim 5 wherein said first chamber in cross-section when inflated, has axial length substantially greater than radial width.

15. A device according to claim 5 wherein said first chamber in cross-section when inflated has axial length substantially less than said radial width.

16. A device according to claim 3 wherein said canopy and first and second chambers are generally symmetrical.

17. A device for intubation of a tracheal passage and operable with an external source of fluid and with a gas flow outward through said passage from the lungs to the atmosphere, the device comprising a tube having a diameter less than that of a normal tracheal passage, and having a distal end for insertion into said tracheal passage and an opposite proximal end, and a canopy of flexible material which is both distendible to a generally annular shape for sealing the space between the tube and the passage and also is collapsible, the canopy having a top part including therein an aperture traversed by said tube, the aperture defining a top edge secured to the outer surface of said tube in an air-tight seal at a first axial position thereon, and also having a body part extending from said top edge and terminating in a distal edge secured to said tube at a second position axially distal from said first position, said body further including inflatable first chamber means for distending said canopy to a generally annular shape which, when distended, defines a dome opening toward said distal end, and within said dome a second generally annular chamber, said body part including at least one aperture near said distal end providing an opening in the bottom of said canopy, said device further comprising inflation means for communicating said source of fluid to said first chamber means for inflating same and thereby distending said canopy, into said dome shape, said canopy also being distendible by said gas flow entering said opening in the bottom of the canopy and filling said second chamber, which thereby distends said canopy into said dome shape, said first and second chambers being inflatable both jointly, and independently of each other, for distending said canopy.

18. A device for intubation of a tracheal passage and operable with an external source of fluid and with a gas flow outward through said passage from the lungs to the atmosphere, the device comprising a tube having a diameter less than that of a normal tracheal passage, and having a distal end for insertion into said tracheal passage and an opposite proximal end, a canopy of flexible material which is both distendible to a generally annular shape for sealing the space between the tube and the passage and also collapsible, the canopy having a top part including therein an aperture traversed by said tube, the aperture defining a top edge secured to the outer surface of said tube in an air-tight seal at a first axial position thereon, said canopy further comprising a body part extending from said top edge and terminating in a free distal edge, the canopy when distended defining a dome and within said dome a generally annular-shaped inner chamber, with said distal edge of the canopy being radially spaced from the tube and having diameter greater than the outer diameter of the tube adjacent thereto and thus defining an annular, open bottom end of said canopy, said canopy being distendible by said outward gas flow in the direction of distal toward proximal, which enters said open bottom end and fills said inner chamber, the body part of said canopy further including an outer generally annular chamber which is inflatable for distending said canopy, inflation means for communicating said source of fluid to said outer chamber for inflating same and thereby distending said canopy, and flexible restraining means of generally fixed maximum length interconnecting said distal edge and said tube at a second position on the tube axially distal of said first position for restraining said distal edge from axial movement toward the proximal end and away from said second position, any distance greater than said fixed length, said inner and outer chambers being inflatable both jointly, and independently of each other, for distending said canopy.

19. A device according to claim 17 wherein said distal edge is secured in an air-tight seal at said second axial position.

20. A device according to claim 1 wherein said first chamber means comprises first and second walls, which form at least one inflatable pocket means defining a generally annular shape, said walls having distal parts joined together in an air-tight seal, and proximal parts spaced apart and each joined to said tube in an air-tight seal.

* * * * *

UNITED STATES PATENT AND TRADEMARK OFFICE
CERTIFICATE OF CORRECTION

PATENT NO. : 3,995,643
DATED      : December 7, 1976
INVENTOR(S) : Abraham D. Merav It is certified that error appears in the above-identified patent and that said Letters Patent are hereby corrected as shown below:

Column 2, line 7, after "Miller et al", "." should read --,--;
         line 8, after "Westgate et al", "." should read --,--;

Column 5, line 26, "FIGS." second appearance should read -- FIG. --;

Column 6, line 2, after "FIG. 8" insert --,--;
         line 3, after "44" delete "," and after "11" insert --,--.

Signed and Sealed this

Seventh Day of February 1978

[SEAL]

Attest:

RUTH C. MASON
Attesting Officer

LUTRELLE F. PARKER
Acting Commissioner of Patents and Trademarks